Figure 1:
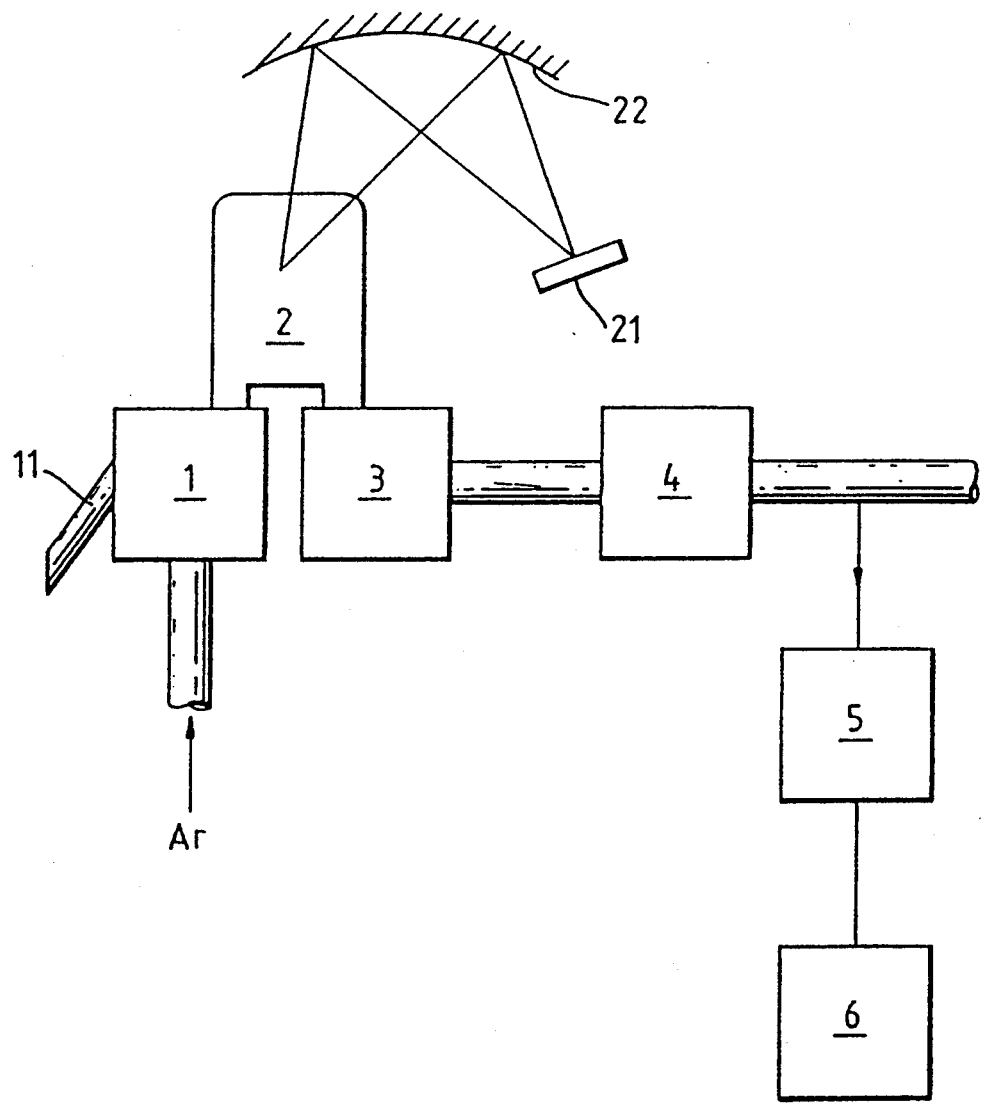

United States Patent [19]

Eastgate et al.

[11] Patent Number: 5,369,035
[45] Date of Patent: Nov. 29, 1994

[54] METHOD AND APPARATUS FOR ANALYTICAL SAMPLE PREPARATION

[75] Inventors: Alan R. Eastgate; Wilfried Vogel, both of Cully, Switzerland

[73] Assignee: Fisons plc, Ipswich, England

[21] Appl. No.: 969,228

[22] PCT Filed: Aug. 7, 1991

[86] PCT No.: PCT/GB91/01345
§ 371 Date: Apr. 2, 1993
§ 102(e) Date: Apr. 2, 1993

[87] PCT Pub. No.: WO92/02282
PCT Pub. Date: Feb. 20, 1992

[30] Foreign Application Priority Data

Aug. 9, 1990 [GB] United Kingdom ............ 9017446.7
Sep. 18, 1990 [GB] United Kingdom ............ 9020315.9

[51] Int. Cl.$^5$ ........................................... G01N 21/62
[52] U.S. Cl. .................................... 436/171; 436/164; 436/173; 436/175; 436/181; 422/82.08; 422/82.09; 356/36; 356/316; 250/281; 250/288; 250/425
[58] Field of Search ............ 436/164, 171, 173, 174, 436/175, 177, 181; 422/82.05, 82.09, 82.08; 356/36, 312, 315, 316; 250/281, 288, 423 R, 425

[56] References Cited

U.S. PATENT DOCUMENTS

| | | | |
|---|---|---|---|
| 2,839,133 | 6/1958 | Brendel | 159/48.1 |
| 3,269,451 | 8/1966 | Mehlo et al. | 159/4.02 |
| 3,398,286 | 8/1968 | Ford et al. | 356/36 |
| 3,438,711 | 4/1969 | Hell | 356/315 X |
| 3,486,836 | 12/1969 | Venghiattis | 356/315 X |
| 3,495,648 | 2/1970 | Amadon | 159/3 |
| 3,632,324 | 1/1972 | Sasaki et al. | 65/43 |
| 3,661,369 | 5/1972 | Costello | 432/32 |
| 3,740,145 | 6/1973 | Mitchell | 356/315 |
| 4,112,297 | 9/1978 | Miyagi et al. | 250/288 |
| 4,201,469 | 5/1980 | Matousek et al. | 356/312 X |
| 4,361,401 | 11/1982 | Smith, Jr. et al. | 356/312 X |
| 4,367,042 | 1/1983 | Smith, Jr. et al. | 356/315 |
| 4,443,105 | 4/1984 | Huber et al. | 356/312 |
| 4,556,318 | 12/1985 | Barnes et al. | 356/316 |
| 4,886,359 | 12/1989 | Berndt | 356/315 X |
| 4,989,976 | 2/1991 | Huber | 356/315 |

FOREIGN PATENT DOCUMENTS

| | | | |
|---|---|---|---|
| 3233130 | 3/1984 | Germany | 356/315 |
| 3424696 | 7/1984 | Germany | |
| 63-25534 | 2/1988 | Japan | |

OTHER PUBLICATIONS

Tambov Chem Equip, "Solid sample atomising device applies laser radiation to sample through window in cell and conical nozzle passes aerosel directly into heated atomiser", SU 1226206, A, Apr. 23, 1986, 8648 (Basic).

Baldin M. N., "Chromatographic molecular condensation nuclei detector has photo-reactor communicating with mixer of condenser by cylindrical channel of broken-line shape to exclude ultraviolet radiation", SU 1154593, A, May 7, 1985, 8546 (Basic).

*Primary Examiner*—James C. Housel
*Assistant Examiner*—Maureen M. Wallenhorst
*Attorney, Agent, or Firm*—Chilton, Alix & Van Kirk

[57] ABSTRACT

In the elemental analysis of an analyte present in a sample by optical or mass spectrometry, a nebulizer sprays the liquid sample into a chamber which has a wall transparent to infra-red radiation. Infra-red radiation from a heater external to the chamber is focused on to the droplets of sample as they emerge from the nebulizer, disrupting the droplets into smaller ones and evaporating solvent from them as they pass through the chamber. The thus desolvated sample stream is delivered into a plasma and the reaction accuracy within the plasma is qualified by the spectrometer.

16 Claims, 1 Drawing Sheet

METHOD AND APPARATUS FOR ANALYTICAL SAMPLE PREPARATION

BACKGROUND OF THE INVENTION

1. Field of the Invention

This invention relates to apparatus and methods for elemental analysis, in particular to pre-treatment of a sample to be analysed.

2. Description of the Prior Art

Elemental analysis encompasses a variety of techniques which involve the qualitative and/or quantitative determination of the elemental composition of a sample based on the atomic properties of the constituent elements.

One such form of elemental analysis is atomic emission spectroscopy (AES), which involves exciting the chemical elements in a sample to emit light of one or more specific wavelengths (spectral light). Atomisation and excitation of the sample occurs in a suitable source, for example, an inductively coupled plasma (ICP). The technique is conventionally applied to a fine dispersion of the sample under investigation. The dispersion may be prepared by various means; spray generators, thermospray systems, pneumatic nebulisers or ultrasonic nebulisers (USNs) may be used in the case of liquid samples; and electric arc heating or laser ablation used in the case of solid samples.

By liquid sample is meant any sample for analysis in which the analyte(s) are present in a liquid carrier, for example, solutions, dispersions, suspensions, colloids and slurries.

In practice it is found that the quality of the analysis depends strongly on the particle size distribution of the dispersion, the presence of larger particles being deleterious in that the atomisation and excitation of such larger particles is less efficient.

In the case of liquid samples it is also desirable that the liquid carrier is evaporated from the dispersed droplets so that the analyte enters the plasma source as an essentially dry aerosol. Evaporation of the liquid is advantageous because it cancels the cooling effect on the plasma caused by the injection of large volumes of liquid, meaning more energy is available for atomisation and excitation; it also reduces other carrier effects such as plasma instability and spectral interferences, for example, oxide interferences when the carrier is water.

Conventional methods of evaporation involve passing the dispersed sample, in a flow of carrier gas, through a heated tube, at for example, 130° C., to evaporate the liquid carrier and then through a refrigerated tube to condense and separate the liquid from the analyte aerosol. In such a process the sample is heated, by conduction, to the boiling point of the droplet over a period of about one second, liquid evaporates leaving the analyte contained therein as a single particle. The resulting particle size is therefore defined by the droplet size and the concentration of analyte in the sample. Thus, even with the fine dispersions produced by, for example, USNs the analyte particles left after evaporation of the liquid may still be larger than is desirable for efficient atomisation and excitation.

SUMMARY OF THE INVENTION

We have now found that the atomic emission analysis of liquid samples can be substantially improved by a rapid radiative heating of the dispersion, so as to evaporate liquid from the dispersion, when the atoms to be analysed for are still entrained in small droplets, and that this technique is also valuable in preparing samples for other methods of elemental analysis.

Thus, according to the invention there is provided an analytical sample pre-treatment apparatus for the production of aerosols from liquid samples comprising
a) means for nebulising the liquid sample to produce droplets, and
b) means for subjecting the droplets so formed to rapid radiative heating so as to evaporate liquid from the sample droplets.

By 'rapid radiative heating' is meant radiative heating of the sample to a temperature above the boiling point of the liquid carrier within a very short time, i.e., the same droplets are caused to explode. The heating time is preferably less than 100 ms and more preferably less than 50 ms. Where the carrier is water, for example, the rapid heating may be such as to heat the sample to a temperature of about 200° C. within 10 ms.

According to a further aspect of the invention there is provided a method for the elemental analysis of a liquid sample, which method comprises the steps of a) nebulising the liquid sample to produce droplets, b) subjecting the droplets so formed to rapid radiative heating so as to evaporate liquid from the sample droplets, and c) analysing the sample aerosol by an appropriate technique.

Appropriate analytical techniques which may be used in the method of the invention include optical emission spectroscopy, atomic absorption spectroscopy, atomic fluorescence spectroscopy and mass spectroscopy. The method of the invention may also be used as a means for coupling liquid chromatography units to any of the aforementioned analytical techniques.

According to another specific aspect of the invention, therefore, there is provided a method for the optical emission analysis of a liquid sample, which method comprises the steps of a) nebulising the liquid sample to produce droplets, b) subjecting the droplets so formed to rapid radiative heating so as to evaporate liquid from the sample droplets, c) exciting the chemical elements in the sample aerosol to emit light, and d) measuring the intensity of the emitted light at one or more wavelengths.

According to another aspect of the invention there is provided an optical emission spectrometer, comprising a) means for nebulising a liquid sample to produce droplets, b) means for subjecting the droplets to rapid radiative heating so as to evaporate liquid from the sample droplets, c) means for exciting the chemical elements in the sample aerosol to emit light, and d) means for measuring the intensity of the emitted light at one or more wavelengths.

Similarly, the scope of the invention includes other analytical techniques (examples of which are given above) and corresponding instruments which are appropriately modified.

The apparatus and method according to the invention are advantageous in that the rapid radiative heating of the sample droplets prevents or inhibits agglomeration of the droplets into larger droplet. This in turn inhibits the formation of relatively large particles of the sample under investigation resulting in improved sensitivity. The rapid radiative heating causes the droplets to 'explode' in the boiling process which may result in the partition of the analyte contained therein into smaller particles, rather than 'drying' slowly leaving all the solid material as a single particle.

An example of the means by which the rapid radiative heating of the sample droplets can be achieved is to place the dispersed sample at one focus of a reflector or a lens and to heat it with a radiation source placed at the other focus.

We prefer the heating to be achieved using a reflector, more preferably an ellipsoidal reflector, particularly an ellipsoidal metal reflector.

The sample droplets may be heated by intense microwave heating at 22.3 GHz (in the case of aqueous liquids). However, we prefer the radiation source to be a heat-bar, i.e., a heating element having a bar-like shape.

The surface of the heat-bar is preferably chosen to be strongly emissive in those regions of the infrared spectrum where the liquid carrier is strongly absorbing. For example, where the carrier is water the heat-bar may have a surface of silicon carbide.

During heating, the sample droplets may be held in a heating chamber, for example, a tube which is transparent to the heating radiation, e.g. a tube of infrared transmissive quartz. The heating chamber may be in the form of a flow-through tube. However, we prefer the heating chamber to be such that re-condensed liquid cannot re-enter the region in which evaporation of the liquid occurs. A suitable form is a vertical tube sealed at one end with both the inlet and the outlet in the other end.

After heating, the sample aerosol may be separated from the evaporated liquid by one or more liquid removal devices, suitable devices include condensers and gas diffusion cells.

BRIEF DESCRIPTION OF THE DRAWING

A preferred embodiment of the invention will now be described, by way of illustration only, with reference to the accompanying drawing in which FIG. 1 is a schematic view of an atomic emission spectrometer.

DESCRIPTION OF THE DISCLOSED EMBODIMENT

An atomic emission spectrometer comprises a sample conduit upon which are sequentially situated a nebuliser (1), a sample heating chamber (2), a condenser (3) and an ICP torch (4).

A liquid sample of the material under investigation is introduced into the nebuliser (1) via a sample inlet port (11) and nebulised i.e. converted to a fine dispersion. The conduit is flushed with argon gas from a pressurised cylinder (not shown) such that the dispersed sample is carried successively through the heating chamber (2), the condenser (3) and the ICP torch (4).

The heating chamber (2) is located at one focus of an ellipsoidal reflector (22). In the heating chamber (2) the sample is subjected to rapid radiative heating by means of a heat-bar (21) located at the other focus of the reflector (22). The surface of the heat-bar (21) is chosen to be strongly emissive in those regions of the infrared spectrum at which the liquid carrier of the sample is strongly absorbing. The heating chamber (2) comprises a tube of material which is transparent at these wavelengths, and is in the form of a vertical tube sealed at the top with both the inlet and the outlet in the base.

After heating, and evaporation of liquid from the sample, the sample aerosol passes through the condenser (3) where the sample analyte is separated from the evaporated carrier. The sample aerosol then passes into the ICP torch (4) where it is excited to emission at temperatures of 4,000 to 8,000K.

The emitted light is dispersed by a monochromator (5) and its intensity at the wavelength of interest is measured by a detector (6).

The nebuliser (1), condenser (3), ICP torch (4), monochromator (5) and detector (6) may be of conventional design.

We claim:

1. Apparatus for the elemental analysis of an analyte present in a liquid sample, said apparatus comprising:

means for nebulizing a liquid sample to produce droplets therefrom;

means for radiantly heating said droplets to evaporate liquid therefrom, said radiant heating means comprising a source of radiant energy and means for focusing said radiant energy provided by said source on to at least some of said droplets, said source of radiant energy being of sufficient power to cause heating of said droplets to above their boiling point in less than 100 ms to thereby cause the droplets produced by said nebulizing means to explode into smaller droplets before the liquid is completely evaporated, each said smaller droplet containing a smaller quantity of the analyte than contained in the droplet from which it is formed;

a plasma source for generating a plasma, said plasma source being disposed to receive said smaller droplets, said plasma reacting with said smaller droplets to produce emissions which are characteristic of at least one element present in said analyte; and analyzing means responsive to said emissions for identifying said at least one element present in said analyte.

2. The apparatus of claim 1 further comprising a condenser for removing evaporated liquid from the flow of smaller droplets being fed from said heating means to said plasma source.

3. The apparatus of claim 1 wherein said heating means further includes a heating chamber, the walls of said chamber being substantially transparent to the radiation generated by said source of radiant energy, said source of radiant energy being disposed outside said chamber.

4. The apparatus of claim 3 wherein said focusing means includes a reflector, said reflector having a pair of focal points, said source of radiant energy being positioned at a first of said reflector focal points, said droplets emerging from said nebulizing means being located at the other of said reflector focal points.

5. The apparatus of claim 4 wherein said source of radiant energy comprises a heat-bar and said reflector is an ellipsoidal metal reflector.

6. The apparatus of claim 4 wherein said source of radiant energy comprises a heater having a surface of silicon carbide.

7. The apparatus of claim 1 wherein said source of radiant energy comprises a heater having a surface of silicon carbide.

8. The apparatus of claim 1 wherein said analyzing means comprises means responsive to optical emissions from said plasma.

9. The apparatus of claim 1 wherein said analyzing means comprises an atomic absorption spectrometer.

10. The apparatus of claim 1 wherein said emissions comprise light energy and said analyzing means comprises an atomic fluorescence spectrometer.

11. The apparatus of claim 1 wherein said emissions comprise ions and said analyzing means comprises a mass spectrometer.

12. A method for the elemental analysis of an analyte present in a liquid sample, said method comprising the steps of:
   (a) nebulizing said liquid sample to produce droplets therefrom;
   (b) subjecting the droplets so formed to radiant heat to evaporate liquid therefrom;
   (c) generating a plasma and introducing the heated droplets into said plasma; and
   (d) analyzing for at least one element present in said analyte by utilizing the optical emission, atomic absorption or atomic fluorescence spectroscopy of the radiation emitted by said plasma, or by utilizing the mass spectroscopy of ions produced in said plasma;
   wherein
   (i) in step (b), the droplets are subjected to radiant heat from a source of radiant heat; and
   (ii) said source of radiant heat has sufficient power to heat said droplets to above their boiling point in less than 100 ms, thereby causing the droplets produced in step
   (a) to explode into smaller droplets before the liquid is completely evaporated, each said smaller droplet containing a smaller quantity of the analyte than contained in the droplet from which it is formed.

13. The method of claim 12 further comprising the step of passing the smaller droplets through a condensor to remove evaporated liquid before introduction of the smaller droplets into the plasma.

14. The method of claim 12 wherein step (b) is carried out in a chamber, the walls of which are transparent to said radiant heat, and the source of radiant heat is disposed outside said chamber.

15. The method of claim 14 wherein radiant heat is focused in step (b) on the droplets by a reflector having a pair of focal points, the reflector being disposed so that the droplets produced in step (a) are located at one focus of the reflector and the source of radiant heat is located at the other focus of the reflector.

16. The method of claim 12 wherein the source of radiant heat comprises a heater having a surface of silicon carbide.

* * * * *